United States Patent [19]

Stromer

[11] Patent Number: 5,304,207
[45] Date of Patent: Apr. 19, 1994

[54] ELECTROSTIMULATOR WITH LIGHT EMITTING DEVICE

[76] Inventor: Merrill Stromer, 8924 N. 65th St., Paradise Valley, Ariz. 85253

[21] Appl. No.: 831,163

[22] Filed: Feb. 5, 1992

[51] Int. Cl.$^5$ .......................... A61N 1/00; A61N 1/18; A61N 1/40
[52] U.S. Cl. .......................................... 607/3; 607/46; 607/88; 607/145
[58] Field of Search ............ 128/419 R, 419 S, 419 C, 128/783, 798, 800, 802, 395, 907, 421, 422, 362, 396, 420 R, 420 A, 786, 803, 632–633; 606/32, 42; 600/13, 14; 604/20; 273/84 ES; 361/232, 225; 33/233; 231/7; 607/46, 88, 90

[56] References Cited

U.S. PATENT DOCUMENTS

| | | | |
|---|---|---|---|
| 4,112,923 | 9/1978 | Tomecek | 128/419 R X |
| 4,305,390 | 12/1981 | Swartz | 128/362 X |
| 4,486,807 | 12/1984 | Yanez | 273/84 ES |
| 4,535,784 | 8/1985 | Rohlicek et al. | 128/907 X |
| 4,694,840 | 9/1987 | Kairis et al. | 128/907 X |
| 4,763,657 | 8/1988 | Chen et al. | 128/422 |
| 4,846,044 | 7/1989 | Lahr | 361/232 X |
| 4,917,092 | 4/1990 | Todd et al. | 128/421 |
| 4,949,721 | 8/1990 | Toriu et al. | 128/421 |
| 4,968,034 | 11/1990 | Hsieh | 273/84 ES |
| 4,977,895 | 12/1990 | Tannenbaum | 128/421 |
| 4,989,605 | 2/1991 | Rossen | 128/422 |
| 5,024,236 | 6/1991 | Shapiro | 128/395 X |
| 5,133,352 | 7/1992 | Lathrop et al. | 128/419 R |

OTHER PUBLICATIONS

Colov, H. C., "Low Level Laser Biomodulation for Chronic Pain Management," *Contemporary Issues in Chronic Pain Management*, Kluwer Academic Publishers, 1991, pp. 287–295.
Kleinkort, J. A. and R. A. Foley, "Laser Acupuncture: Its Use in Physical Therapy," *American Journal of Acupuncture*, vol. 12, No. 1, 1984, pp. 51–56.
Soric, R. and M. Devlin, "Transcutaneous Electrical Nerve Stimulation-Practical Aspects and Applications," *Postgraduate Medicine*, vol. 78, No. 4, Sep. 15, 1985, pp. 101–106.
Walker, J. "Relief from Chronic Pain by Low Power Laser Irradiation", *Neuroscience Letters*, vol. 43, 1983, pp. 339–344.

Primary Examiner—Richard J. Apley
Assistant Examiner—John P. Leubecker

[57] ABSTRACT

An improved electrostimulator apparatus, comprises first and second electrodes spaced-apart a predetermined distance, an electrical signal generator for providing pulses of predetermined width and repetition rate to the spaced-apart electrodes, and an LED providing a beam of light projecting between the spaced-apart electrodes toward the object intended to be electrostimulated. The electrodes have substantially co-planar external faces approximately perpendicular to the light beam. The electrodes, signal generator and LED are mounted in an elongated housing having a longitudinal central axis. The electrodes are exposed on an end and the light beam is emitted from the same end and substantially parallel to the central axis. An ON/OFF switch actuates the signal generator and the LED when turned ON. It automatically turns OFF state when released so that the signal generator and the LED are always ON or OFF together.

18 Claims, 1 Drawing Sheet

ELECTROSTIMULATOR WITH LIGHT EMITTING DEVICE

FIELD OF THE INVENTION

The present invention relates to electrostimulators, that is, apparatus adapted to provide a mild electrical shock for therapeutic, palliative or other purposes.

BACKGROUND OF THE INVENTION

Electrostimulation is a well known technique for treatment of various medical conditions. Electrostimulation involves providing a mild electrical shock to particular regions of a human (or other) body. Such treatment is useful, among other things, in pain therapy and has been shown to provide relief from chronic pain under circumstances when other methods have failed or lost their efficacy. Electrostimulation is believed to block transmission of nerve pulses thereby interrupting the flow of "pain" signals along the body's nervous system. While electrostimulation of this type does not provide a cure to the underlying cause of pain, it is a useful palliative which can be very helpful to those who suffer from chronic pain. The term TENS, standing for Transcutaneous Electrical Nerve Stimulation, has been coined in the art to refer to this type of pain relief by electrostimulation. See for example, Soric and Devlin, "Transcutaneous Electrical Nerve Stimulation-Practical Aspects and Applications," *Postgraduate Medicine*, Vol. 78, No. 4, Sep. 15, 1985, pages 101–106.

While the present invention is described for convenience of explanation in terms of use in connection with TENS treatment, those of skill in the art will understand based on the description herein that other uses may also be made of the present invention, and that it is not limited to TENS and may be applied to electrostimulation in general.

TENS equipment exists but suffers from a number of limitations well known in the art. For example, much of present day TENS equipment is bulky or requires placement of needle electrodes or other separate electrodes taped to the body and connected by wires to the TENS apparatus. This makes treatment inconvenient or creates risk of infection and often requires that it provided by trained medical personnel. In other cases, even with TENS equipment having integral electrodes, it is difficult to direct the electrodes to the precise region of the body desired to be stimulated because as the electrodes are brought in contact with the body the gap therebetween across which the electrical stimulation signal is provided is hidden by the electrodes and/or the body of the TENS device. Thus, there continues to be a need for improved TENS and other electrostimulator devices which are more convenient, of a size and shape that may be easily held and manipulated even by persons of limited dexterity, are simple to operate, are easier to direct to the target stimulation region, and are effective in achieving the objectives of the electrostimulation, as for example, pain relief.

SUMMARY OF THE INVENTION

There is provided an electrostimulator apparatus, comprising most generally, first and second electrodes spaced-apart a predetermined distance, electrical signal generating means for providing electrical signals of predetermined energy and repetition rate to said spaced-apart electrodes, and light emitting means providing a beam of light projecting between said spaced-apart electrodes toward the object intended to be electrostimulated.

It is desirable that the first and second electrodes have substantially co-planar external faces approximately perpendicular to the beam of light. In a preferred embodiment, the electrodes, signal generating means and light emitting means are mounted in a common housing, for example, an elongated tube having a longitudinal central axis. The electrodes are exposed on a first end thereof at one extremity of the central axis and the light beam is emitted from the same first end and substantially parallel to the central axis.

In the preferred embodiment there is provided an ON/OFF switch which actuates the signal generating means and the light emitting means when placed in the ON state and which automatically returns to the OFF state when released so that the signal generating means and the light emitting means are always ON or OFF together. The light emitting means is conveniently a light emitting diode.

BRIEF DESCRIPTION OF THE DRAWINGS

FIGS. 4–6 are perspective views of the electrostimulator of FIG. 2 as it is brought closer and closer to an intended stimulation region;

DETAILED DESCRIPTION OF THE PREFERRED EMBODIMENT

Figure 1:
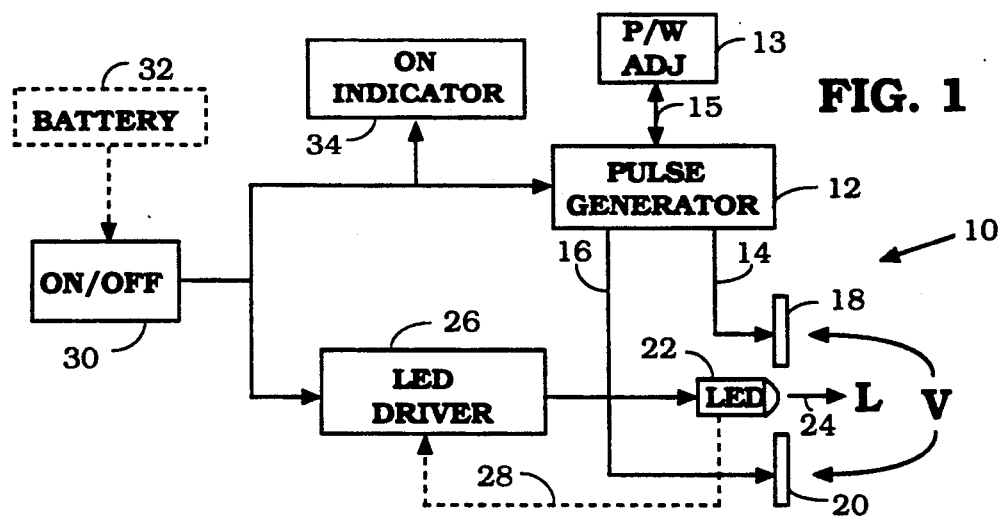
FIG. 1 is a simplified schematic block diagram of an electrostimulator according to the present invention.

FIG. 1, is a simplified schematic block diagram of electrostimulator 10 according to a preferred embodiment of the present invention. Electrostimulator 10 has electrical signal generator 12 having outputs 14, 16 coupled to spaced-apart electrodes 18, 20, respectively. Signal generator 12 desirably produces pulsating voltage V across electrodes 18, 20. It is preferred that the output voltage delivered to electrodes 18, 20 be about 150 volts, no load. When electrostimulator 10 is battery operated, this voltage is conveniently obtained by means of an induction coil or step-up transformer included in signal generator 12. The pulses provided by signal generator 12 are desirably unidirectional rather than of alternating polarity, but this is not essential and alternating current signals may also be used. Electrical generator circuits capable of generating a wide variety of pulse shapes, repetition rates and uni-directions or bi-directional current flow are well known in the art and may be constructed using readily available commercial components. Surface mount components are preferred when it is desired to minimize the space occupied by the electrical signal generator.

A pulse repetition rate of about 100 Hz or less is useful, with about 80 Hz or less being convenient, and with about 45 Hz being preferred, but larger or smaller repetition rates can also be used. Pulse widths of about 1 to 100 microseconds are useful, with about 3-80 microseconds being preferred. Pulse width is conveniently adjusted using pulse width adjustment control 13 coupled to signal generator 12 by connection 15. A potentiometer is suitable for adjustment control 13.

Varying the pulse width has the effect of varying the charge which flows through the body as a result of the electrostimulation. The greater the charge, the greater the tingling sensation and the greater the effect. A pulse width control or other means of controlling the electrostimulation is highly desirable since it was found that there is substantial variation from individual to individual in the amount of electrical stimulation needed to achieve a certain pain inhibiting result and also great variation in the individual tolerance to electrostimulation. A charge which one person may hardly feel and which has little effect can cause significant discomfort and great effect in another person. Thus, a feature of the present invention is the provision of the electrostimulation charge variation which is conveniently accomplished through pulse width control, in combination with the other features described herein. Other means of varying the electrostimulation charge may also be used. Non-limiting examples are, varying the pulse voltage, varying the pulse repetition rate and varying the pulse waveform.

The current flowing through the body between electrodes 18, 20 as a result of the electrostimulation varies according to the conductivity of the body region being excited and the contact resistance between the electrodes and the skin. The contact resistance is conveniently minimized using a standard conductive gel such as is used in connection with electrocardiogram leads and other leads for body electrical measurements. Such gels are well known in the art. Spectra-360 ™ type electrode gel manufactured by Parker Laboratories, Inc., of Orange, N.J., 07050 is an example of a suitable gel.

Current flow during the pulses depends typically on the resistance presented between the electrodes and varies from a high of about 90 milliamps for a 500 Ohm load to about 10 milliamps for a 10,000 Ohm load. The charge delivered per pulse is typically about 5 microCoulombs for a 500 Ohm load dropping to about 0.5 microCoulomb for a 10,000 Ohm load. For a fixed excitation, the current pulse width through the body generally decreases as load resistance decreases due to circuit loading. The current pulse magnitude also decreases as the supply voltage decreases.

Electrostimulator 10 further comprises light source 22 emitting light beam 24, indicated by the letter L. Light source 22 may be any convenient light source, but a light emitting diode (LED) is especially suitable because of its typical small size and suitable wavelength for penetrating radiation, e.g., 600-1000 nanometers, conveniently 600-800 nanometers and preferable about 670+/−10 nanometers. LED's having output powers of less than 1 milliWatt are preferred. Higher or lower powers can be used depending upon the particularly desired result. As used hereinafter, the term LED is intended to include light sources of any form or type suitable for the intended application, including but not limited to light emitting diodes. While it is preferable that the light output be continuous, this is not essential and the LED may be pulsed so as to provide a pulsating light beam. A repetition rate above about 20 Hz is desirable.

Light source 22 is excited by light source driver 26. Light source drivers are well known the art. It is preferred to use a constant emittance type driver, that is, one that takes advantage of a sensor coupled to the light source for measuring the optical output, i.e., the emittance. The sensor signal is fed back to driver 26, as indicated by dashed line 28, so that driver 26 excites light source 22 to have a constant predetermined light output over a wide range of supply voltages or other variables. Those of skill in the art will understand how to provide such an arrangement based on standard components.

Electrostimulator 10 further conveniently has ON/OFF switch 30 coupled between power source 32 (e.g. a battery) and pulse generator 12 and LED driver 26. "ON" indicator light 34 showing when pulse generator 12 and LED driver 26 are energized is desirable but not essential. This is convenient in the situation when the light beam 24 from LED 22 cannot be readily seen because it is being absorbed in the body against which electrodes 18, 20 are being pressed.

Figure 2:
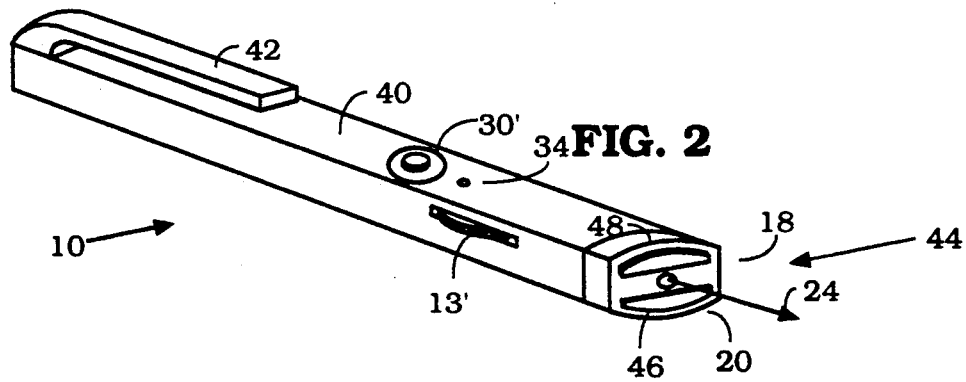
FIG. 2 is a perspective view of the exterior of an electrostimulator according to the present invention.

FIG. 2 shows a perspective view in simplified form of the external appearance and arrangement of electrodes and light beam of electrostimulator 10. Electrostimulator 10 preferably has elongated housing 40 having a longitudinal central axis substantially aligned with light beam 24. Electrodes 18, 20 are spaced apart and exposed on end 44 of housing 40. Window 46 is provided in end portion 48 of housing 40 through which light beam 24 emerges so as to extend away from end 44. It is desirable that electrodes 18, 20 protrude by a small amount from end portion 48. Voltage V (see FIG. 1) appears across electrodes 18, 20. Electrodes 18, 20 are conveniently of conductive non-poisonous materials which do not produce allergic reactions on the skin. Non-limiting examples are, stainless steel, gold, platinum, and carbon, but other suitable materials may also be used. Titanium is preferred.

Window 46 is transparent to light beam 24. As will be subsequently explained it is desirable that end portion 48 also be transparent. Clear plastic is suitable but clear glass or crystal may also be used. Housing 40 may be of any convenient material of suitable strength. Molded plastic is suitable, but metal may also be used. Housing 40 is hollow so as to accommodate the elements shown in FIG. 1.

Exposed on housing 40 is push-button 30' of ON/OFF switch 30. Also exposed on housing is adjustment knob or wheel 13' for pulse width adjustment means 13. "ON" indicator lamp 34 is also visible on housing 40. Housing 40 also desirably has pocket clip 42 so that electrostimulator 10 may be readily retained in the user's or physicians or therapist's pocket.

While the illustrated shape and arrangement of the parts of electrostimulator 10 is preferred, other convenient arrangements may also be used. For example, and not intended to be limiting, electrostimulator 10 can be cylindrical, spherical, box-shaped, polygonal shaped, or any other shape desired by the user. What is important is that (a) electrodes 18, 20 have exposed faces mounted in relatively close proximity yet spaced apart, and (b) that light beam 24 emerge from between the spaced apart electrodes. It is also desirable that the exposed faces of electrodes 18, 20 slighlty protrude from housing 40. This arrangement provides a particularly convenient and effective electrostimulator.

Figure 3:
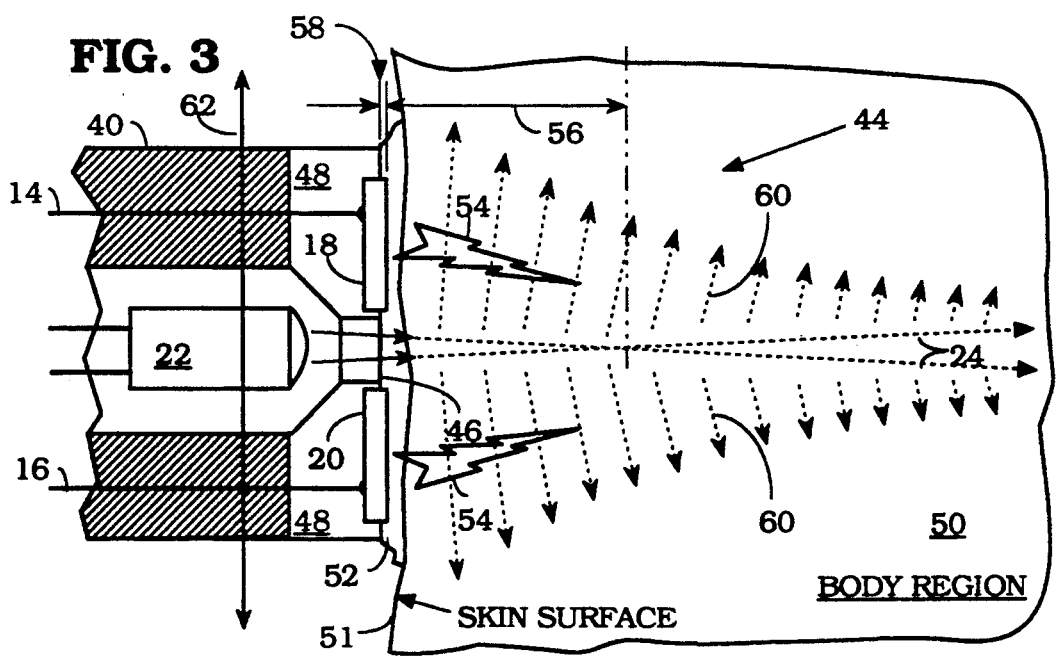
FIG. 3 is a partial cut-away and cross-sectional view of a portion of the electrostimulator of FIG. 2 when in contact with a body desired to be stimulated.

FIG. 3 is a partial cut-away and cross-sectional view showing end portion 48 of body 40 of electrostimulator 10 when in contact with body 50 as it is being used. Electrodes 18, 20 are in contact with skin 51 of body 50 or separated therefrom by at most a thin layer of conductive gel 52. When switch 30 is energized, pulses 54 are applied to body 50 as illustrated pictorially by 54, at the same time that light beam 24 from LED 22 is penetrating into body 50.

Light beam 24 is desirably arranged to focus at distance 56, e.g., generally 2-15 mm and preferably about 6-8 mm, ahead of electrodes 18, 20 which protrude by small amount 58, e.g., about 0.1-0.8 mm from end face 44. Window 46 may be curved to also function as a lens to facilitate the desired focus. Beyond focal distance 56, light beam 24 desirably diverges. This is unlike conventional prior art light pointers. Conventional light pointers used for illustrating talks or lectures are well known in the art. They have their light output collimated into a narrow beam focussed as close to infinity as is possible so as to produce a narrow pencil of light which when pointed at a screen or display provides a small easily visible spot for the purpose of indicating or identify that portion of the screen or display that the audience should consider.

As indicated by arrows 60, light beam 24 penetrates and is scattered within body 50. The depth of penetration of the light beam depends upon its wavelength. For example, at wavelengths of about 670+/−10 nanometers, light beam 24 readily penetrates about 10-15 mm or more into body region 50. As is explained in more detail in connection with FIGS. 7-8, it is desirable that end portion 48 of housing 40 also be transparent. When electrostimulator 10 is energized, it is desirably moved over the skin as indicated by arrow 62 about the location where electrostimulation is desired to be accomplished. As those of skill in the art appreciate, the nerve sites to which the electrostimulation is intended to be applied are generally subcutaneous, that is at some depth below the user's skin.

In order to obtain the maximum pain blocking effect with minimum discomfort to the patient, it is generally desirable to apply the electrostimulation to precise locations. The present invention is especially well adapted to accomplish precise location of the electrostimulation. This is illustrated in FIGS. 4-8.

FIGS. 4-6 show electrostimulator 20 emitting light beam as it is brought into proximity with skin region 51 of body 50 having an intended electrostimulation target indicated by spot 64. Spot 64 may be a visible skin feature which fortuitously overlies a desired electrostimulation sensitive area or a mark deliberately placed there by the health care worker as an aid in placing the electrostimulator in the right position. The problem with ordinary electrostimulators is that the closer one brings them to the skin, the more difficult it is to tell if they are going to contact the correct spot. The present invention overcomes this difficulty by use of light beam 24.

Light beam 24 greatly facilitates placing the electrostimulator precisely on target 64. In FIG. 4, while electrostimulator 10 is still at a considerable distance from body 50, light beam 24 is centered on target 64. In FIGS. 5 and 6, as electrostimulator 10 is brought closer and closer to body 50, light beam 24 is maintained by visual observation on target spot 64 thus guiding electrostimulator 10 to exactly the desired location.

Figure 7:
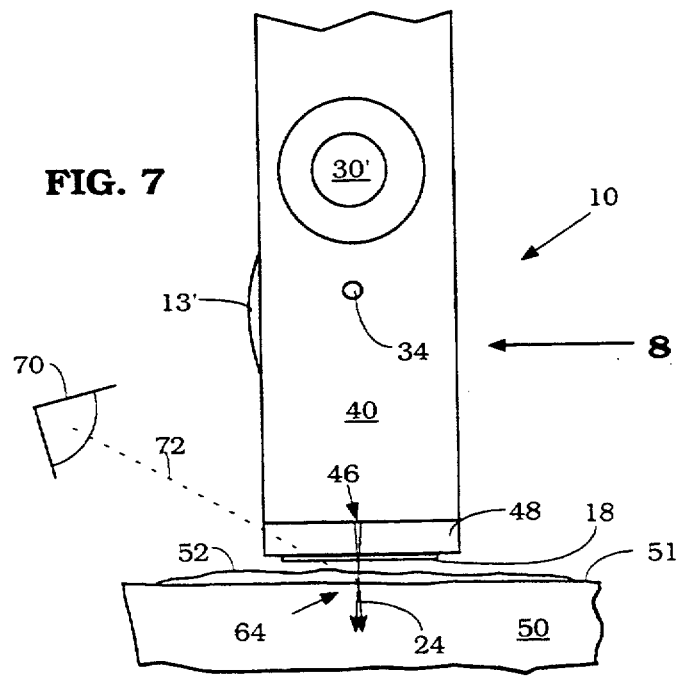
FIG. 7 is a front view of the lower portion of the electrostimulator of FIG. 2 as it is brought into close proximity with an intended stimulation region.
Figure 8:
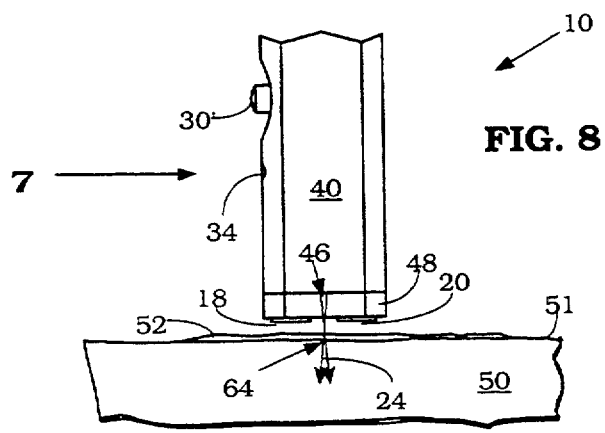
FIG. 8 is a side view of the lower portion of the electrostimulator of FIG. 3 as it is brought into close proximity with an intended stimulation region.

FIGS. 7-8 illustrate the final stages of the targeting process where electrostimulator 10 is almost in contact with skin 51 of body 50. FIG. 7 is a front view of the lower portion of electrostimulator 10 as it is brought into close proximity with skin 51 of body 50 and FIG. 8 is a side view of the same situation. Like reference numbers are used to identify like features in these and the other figures. Gel 52 is desirably in place on skin 51 and electrodes 18, 20 are about to make contact. In order to insure that light beam 24 is still aimed at target 64, end region 48 of housing 40 of electrostimulator 10 is desirably of a substantially clear transparent material. In this way, the user, as illustrated by eye 70 can look along line-of-sight 72 through end region 48 from the side of unit 10 and see that light beam 24 remains on target 64 as the separation between electrostimulator 10 and skin surface 51 is reduced to zero. In this way, more exact placement of electrostimulator 10 is greatly facilitated. Once in place, electrostimulator 10 can be left motionless or moved back and forth as the therapist desires. It is desirable that the LED be on during electrostimulation. This feature is provided by the invented arrangement.

Having described the invention those of skill in the art will appreciate that the arrangement of the present invention provides an improved electrostimulator. The light beam emerging from between the spaced apart electrodes provides a valuable aiming feature which greatly facilitates exact placement of the electrostimulation with respect to the desired nerves or other body feature to be affected. The therapist can mark the desired location and then by aiming the light beam at the mark, and bringing the unit into contact with the skin while maintaining the light beam on the mark, provide precise placement of the unit.

Further, by using light wavelengths that penetrate skin and flesh, the light energy is delivered to substantially the same sub-cutaneous region where electrostimulation is occurring, for whatever palliative or other effect the combination may, in the experience of the user provide, depending upon the individual and the condition being treated. In this respect there is evidence that merely exposing pain control centers to certain wavelengths of light with no electrostimulation can provide relief from pain in some persons as well as changes in body chemistry. For example, in an article entitled, "Relief From Chronic Pain by Low Power Laser Irradiation," appearing in *Neuroscience Letters*, Vol. 43, (1983) pages 339-344, J. Walker reports the results of a double-blind study in which chronic pain sufferers had various body regions irradiated by a 1 multiWatt low power laser operating at 632 nanoMeters with a pulse repetition rate of 20 Hz. Walker states that 19 of 26 subjects experienced significant pain relief. This was accompanied by a substantial change in urinary excretion of 5-hydroxyindoleacetic acid, which Walker states is a degradation product of serotonin. Other effects of light therapy are reported by H. C. Colov in "Low Level Laser Biomodulation for Chronic Pain Management," in *Contemporary Issues in Chronic Pain Management*, Edited by W. C. V. Parris, Kluwer Academic Publishers, Boston, 1991.

While the present invention has been described for convenience of explanation in terms of particular structures and arrangements and circuits and materials, those of skill in the art will appreciate based on the description herein that many variations can be made without departing from the spirit of the present invention. Thus, it is intended to include these and such other variations as will occur to those of skill in the art based on this disclosure in the claims that follow.

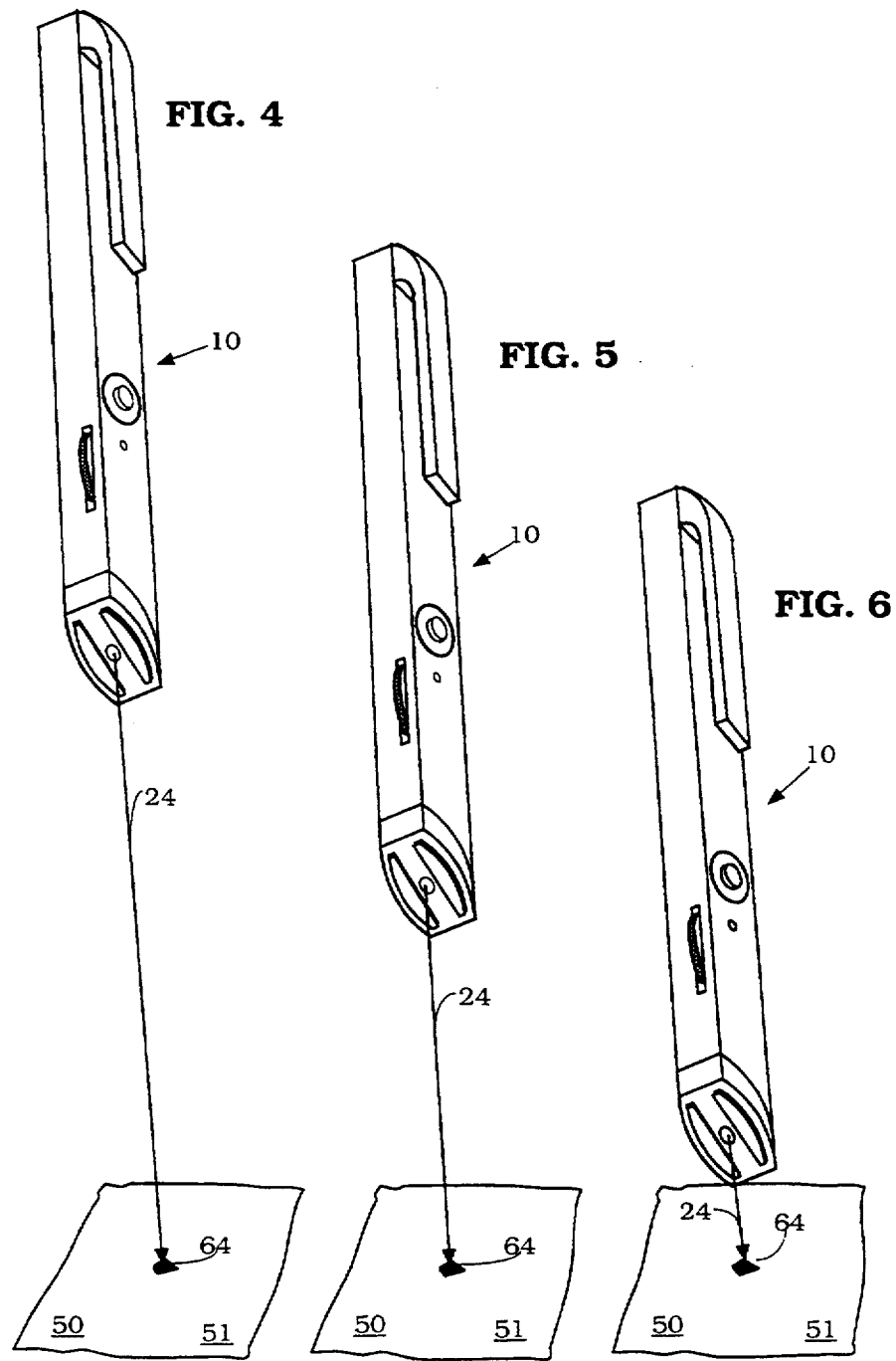

What is claimed is:

1. A non-incapacitating electrostimulator apparatus, comprising:
   a housing;
   first and second electrodes supported by and exposed on the housing so as to be spaced apart a predetermined fixed distance;
   electrical signal generating means supported by the housing for providing varying electrical signals to said spaced apart electrodes, said electrical signals having an amplitude of no greater than approximately 150 volts; and
   light emitting means supported by the housing for focusing a beam of light in a region traversed by a line passing between said spaced apart electrodes.

2. The apparatus of claim 1 further comprising means for varying the electrical charge delivered by the electrical signal generating means to the electrodes.

3. The apparatus of claim 2 wherein the means for varying the electrical charge delivered by the electrical signal generation means comprises pulse width modulation means for varying the width of pulsed electrical signals.

4. The apparatus of claim 1 wherein the first and second electrodes support have substantially planar exposed first faces fixed substantially in a common plane, wherein said common plane is approximately perpendicular to the beam of light.

5. The apparatus of claim 1 wherein the apparatus comprises an elongated barrel containing the signal generating means and the light emitting means and having a longitudinal central axis, and wherein the electrodes are exposed on a first end of the housing at one extremity of the central axis and the light beam is emitted from said first end of said housing and substantially parallel to the central axis.

6. The apparatus of claim 1 further comprising an ON/OFF switch which actuates the signal generating means and the light emitting means when placed in the ON state and automatically returns to the OFF state when released so that the signal generating means and the light emitting means are always ON or OFF together.

7. The apparatus of claim 1 wherein the light emitting means is a light emitting diode.

8. The apparatus of claim 7 wherein the light emitting means emits a wavelength in the range of about 600 to 1000 manometers.

9. The apparatus of claim 1 wherein the light emitting means is a light emitting diode emitting less than about 1 milliwatt.

10. The apparatus of claim 1 wherein the signals are pulsed signals with a repetition rate of less than about 50 Hz.

11. The apparatus of claim 10 wherein the pulsed signals have a pulse width in the range of about 1 to 100 microseconds.

12. A non-incapacitating electrostimulator comprising:
    a housing;
    circuit means for generating an electrical signal, said electrical signal having an amplitude of no greater than approximately 150 volts;
    electrodes supported by the housing so as to have exposed spaced apart principal faces, wherein the electrodes are electrically coupled to the circuit means for transmitting said electrical signal to a region of an external body; and
    a light source mounted in the housing; and
    window means for focusing a beam of light in a region traversed by a line passing between the exposed spaced apart principal faces of the electrodes to the region of the external body.

13. The electrostimulator of claim 12 wherein the exposed spaced apart principal faces of the electrodes are fixed substantially tangent to a common plane.

14. The electrostimulator of claim 13 wherein said light source is located so as to direct said beam of light substantially perpendicular to said common plane.

15. The electrostimulator of claim 14 wherein said light beam is focused beyond said common plane.

16. The electrostimulator of claim 12 further comprising control means for actuating the light source and circuit means simultaneously.

17. An apparatus for simultaneously applying non-incapacitating electrical stimuli and light to a region of a body, comprising:
    a housing having an end comprising a substantially transparent portion;
    spaced apart electrodes having exposed substantially co-planar outer faces mounted adjacent said substantially transparent portion in fixed relationship to each other;
    an electrical signal generator electrically coupled to said spaced apart electrodes for providing time varying electrical stimuli thereto;
    a light emitting means mounted adjacent said end portion and providing a light beam substantially centrally located mid-way between the spaced apart electrodes for providing a guiding light spot indicating the specific interelectrode region to which electrical stimuli will be applied when the spaced apart electrodes are brought in contact with the body with the apparatus activated.

18. The apparatus of claim 17 wherein the light beam forming the guiding light spot is emitted from the apparatus in a direction substantially normal to outer faces of the electrodes.

* * * * *

UNITED STATES PATENT AND TRADEMARK OFFICE
CERTIFICATE OF CORRECTION

PATENT NO. : 5,304,207                                    Page 1 of 3
DATED     : April 19, 1994
INVENTOR(S) : Merrill Stromer et al It is certified that error appears in the above-indentified patent and that said Letters Patent is hereby corrected as shown below:

The drawing sheet, consisting of Fig.4, 5, 6, 7 and 8, should be added as shown on the attached page.

Signed and Sealed this

Twenty-third Day of August, 1994

Attest:

BRUCE LEHMAN

*Attesting Officer*   *Commissioner of Patents and Trademarks*